(12) United States Patent
Kwun et al.

(10) Patent No.: US 7,474,092 B1
(45) Date of Patent: Jan. 6, 2009

(54) METHOD AND DEVICE FOR LONG-RANGE GUIDED-WAVE INSPECTION OF FIRE SIDE OF WATERWALL TUBES IN BOILERS

(75) Inventors: Hegeon Kwun, San Antonio, TX (US);
Hirotoshi Matsumoto, Nagasaki (JP);
James F. Crane, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 11/778,256

(22) Filed: Jul. 16, 2007

(51) Int. Cl.
*G01N 27/82* (2006.01)
*G01N 27/00* (2006.01)
*G01R 33/18* (2006.01)

(52) U.S. Cl. .......... 324/238; 324/240; 73/1.82; 702/35

(58) Field of Classification Search .......... 324/238–240, 324/242–243; 73/1.82, 584, 592, 622–624, 73/650; 702/34–36, 38
See application file for complete search history.

(56) References Cited

U.S. PATENT DOCUMENTS

| | | |
|---|---|---|
| 5,359,898 A | 11/1994 | Latimer |
| 5,526,691 A | 6/1996 | Latimer et al. |
| 5,581,037 A | 12/1996 | Kwun et al. |
| 6,125,703 A | 10/2000 | MacLauchlan et al. |

(Continued)

FOREIGN PATENT DOCUMENTS

GB 2378756 A 2/2003

OTHER PUBLICATIONS

Kwun, Hegeon, Light, Glenn M., "Magnetostrictive sensor technology proven in process applications", Process Plant Maintenance, Oil & Gas Journal, May 22, 2000, p. 77, PennWell Publishing Company.

(Continued)

*Primary Examiner*—Bot LeDynh
(74) *Attorney, Agent, or Firm*—Kammer Browning PLLC

(57) ABSTRACT

Methods and devices for inspecting waterwall tubes for the detection of fire side damage over a long length of the tube are described. The system of the invention uses a magnetostrictive strip and a flat coil-type plate magnetostrictive sensor (MsS) that are held in place on the waterwall using a specially designed frame and an electromagnetic circuit. The magnetostrictive strip and plate type MsS are positioned against a tube in the waterwall using an elastomeric pad or a fluid filled bladder to achieve close contact and good mechanical coupling between the magnetostrictive strip and the tube surface. When current activated, the electromagnet holds the entire assembly in place and provides a DC bias magnetic field required for plate magnetostrictive sensor probe operation. Long-range guided-waves are pulsed into the tube and reflected signals are detected within the same sensor structure. The received signal data representative of a long section of the tube under investigation is then analyzed for the presence of anomalies and defects. When data acquisition for a particular tube or tube section is completed the electromagnet is turned off and the entire device is moved to the next tube in the waterwall.

18 Claims, 4 Drawing Sheets

U.S. PATENT DOCUMENTS

| | | | |
|---|---|---|---|
| 6,164,140 | A * | 12/2000 | Kalinoski .............. 73/861.357 |
| 6,205,859 | B1 | 3/2001 | Kwun et al. |
| 6,497,151 | B1 | 12/2002 | Watts et al. |
| 6,624,628 | B1 | 9/2003 | Kwun et al. |
| 6,925,881 | B1 | 8/2005 | Kwun et al. |
| 6,967,478 | B2 | 11/2005 | Wayman et al. |
| 2003/0183537 | A1 | 10/2003 | Eden et al. |
| 2005/0179430 | A1 | 8/2005 | Park, II et al. |

OTHER PUBLICATIONS

Lebsack, Scott, "Non-invasive inspection method for unpiggable pipeline sections; Unique Pipeline Tool", Pipeline & Gas Journal, Jun. 1, 2002, No. 6, vol. 229; p. 58; ISSN: 0032-0188, Gale Group. Inc., Oildom Publishing Company of Texas, Inc.

Eman, Mohd, Mithin, Abdul-Wahab Al-, Nasser, Emad Al-, "Pilot project on oil gathering system using EMFL and GWUT encourages engineers; External Pipe Inspection Technology; external magnetic flux leakage., guided-wave ultrasonics", Pipeline & Gas Journal, May 1, 2005, No. 5, vol. 232; p. 14; ISSN: 0032-0188, Gale Group, Inc., Oildom Publishing Company of Texas, Inc.

"Rosen detects crack-like defects in gas pipelines: EMAT Crack & Coating Detection ECD; Electromagnetic Acoustic Transducer", Pipeline & Gas Journal, Jul. 1, 2005, No. 7, vol. 232; p. 62; ISSN: 0032-0188, Gale Group, Inc., Oildom Publishing Company of Texas, Inc.

* cited by examiner

METHOD AND DEVICE FOR LONG-RANGE GUIDED-WAVE INSPECTION OF FIRE SIDE OF WATERWALL TUBES IN BOILERS

BACKGROUND OF THE INVENTION

1. Field of the Invention

The present invention relates generally to methods and systems for non-destructive testing and inspection of pipes, tubes, and other longitudinal cylindrical structures. The present invention relates more specifically to methods and systems for accurately positioning long-range torsional guided-wave inspection sensors on waterwall tubes in boiler structures and the like.

2. Description of the Related Art

Most fossil fuel based power generating systems utilize the heat released from burning the fuel to convert water to high pressure steam that is then used to turn a steam turbine connected to an electrical generator. One of the most efficient ways of heating water to convert it to steam involves the use of a waterwall boiler wherein the fuel is burned within a confined furnace space defined by walls made up of an array of water tubes. As relatively cool water passes through the tubes it absorbs the heat from the burning fossil fuel and eventually exits the array of tubes as steam.

The most common cause of forced outage of fossil fuel powered generating units is boiler tube failure. The majority of these failures occur within the furnace waterwall tubes. Various damage mechanisms are known to occur that lead to tube failures through wall loss and cracking. Most of the damage to waterwall tubes occurs on the fire side of the tube by way of wall thinning due to corrosion and/or erosion that results from the furnace exposure and the presence of corrosive gases in the fuel burning process.

To prevent or reduce such boiler tube failures during plant operation, the tubes within such waterwalls are inspected nondestructively during normal outages, typically using ultrasonic wall-thickness measurements. Since the boiler waterwall is a very large structure and ultrasonic wall-thickness measurements are time consuming, thickness measurements are typically taken at several points along the height of the wall. Maintenance decisions regarding the overall condition of the boiler are therefore made based upon a statistical analysis of the very limited measurement data. As a result, the reliability of the current decision making process is less than desired and carries a substantial risk of error. The reliability of the boiler would be significantly improved if the condition of the boiler were determined based on the inspection results of a large portion of the boiler wall, if not the total boiler wall, rather than results from very limited measurement points.

Long-range guided-wave inspection technology is an emerging technology that has the capability of quickly surveying a large volume of a structure for defects and providing comprehensive condition information on the integrity of the structure. Using relatively low frequency (typically under 200 kHz) guided-waves in the pulse echo testing mode, this technology performs a 100% volumetric examination of a large area of a structure and detects and locates internal and external defects in the area around a given test position. In exposed, single tube pipelines, for example, a test range of more than five hundred feet can be achieved in one direction for detecting 2% to 3% defects from a given test position. Percent in such examples refers to the circumferential cross-sectional area of the defect relative to the total pipe or tube cross-section. The guided-wave inspection technology, including the magnetostrictive sensor technology developed at Southwest Research Institute in San Antonio, Tex., is now widely used for testing piping networks in processing plants such as refineries, chemical plants, and power generating stations. The preferred guided-wave mode for pipe or tube inspection is torsional (T) wave mode.

For generalized piping inspection, guided-wave probes that encircle the entire pipe circumference are presently in use. To install a guided-wave probe for piping inspection, the basic systems and methodologies require full access around the pipe circumference with about three to five inches of spacing. When access is limited to only a portion of the piping circumference, the long-range guided-wave inspection method is difficult to apply. Waterwall tubes constructed in boiler furnaces present just such an environment where access to the full circumference of an individual tube is not possible. A typical firewall tube might be constructed from metal components that appear on the outside surface to be an array of closely spaced parallel pipes when; in fact, they most often comprise a unitary structure where no space exists between the pipes forming the wall. An example of a cross-section of a typical firewall tube structure can be seen in FIG. 1 of the present application.

Some efforts have been made in the past to provide sensor structures and methodologies for their use directed to waterwall boiler tubes. As indicated above, such inspections are typically carried out using ultrasonic sensors and methodologies, although the limited range of such sensors requires sampling techniques to be utilized during testing. Other efforts in the field have included those described in the following U.S. patents:

U.S. Pat. No. 5,526,691 issued to Latimer et al. on Jun. 18, 1996 entitled Detection of Corrosion Fatigue Cracks in Membrane Boiler Tubes describes a method for detecting defects and anomalies in boiler tubes arranged in a panel and associated with a waterwall. The system utilizes at least one EMAT (Electromagnetic Acoustic Transducer) coil that generates ultrasonic shear waves at a predetermined beam angle. The method is alleged to provide a better signal-to-noise ratio than conventional ultrasonic techniques and to further eliminate the need for a couplant between the sensor and the boiler tube.

U.S. Pat. No. 6,125,703 issued to Mac Lauchlan et al. on Oct. 3, 2000 entitled Detection of Corrosion Fatigue in Boiler Tubes Using a Spike EMAT Pulsar describes a further EMAT based method for detecting damage in ferromagnetic boiler tube structures using a pair of EMAT coils adjacent the work piece at a non-zero angle with respect to one another. A spike pulse is applied to one of the EMAT coils to generate a horizontally polarized shear wave which is reflected by flaws and defects in the work piece and subsequently received by the second EMAT coil.

U.S. Pat. No. 6,497,151 issued to Watts et al. on Dec. 24, 2002 entitled Non-Destructive Testing Method and Apparatus to Determine Micro Structure of Ferrous Metal Objects describes a method and apparatus for non-destructively investigating structures such as cast iron pipes. A sonic wave in induced in the object and a sensor assembly captures the acoustic signal from the object. The data analysis system calculates the energy of the acoustic wave or calculates the time from its initial induction to determine a nodularity measurement of the metal object.

U.S. Pat. No. 5,359,898 issued to Latimer on Nov. 1, 1994 entitled Hydrogen Damage Confirmation with EMATs describes a method and apparatus for confirming hydrogen damage in boiler tubes that comprises a pair of electromagnetic acoustic transducer coils (EMATS) that are mounted for movement toward and away from each other. An electromagnet produces pulses that generate acoustic waves across a chord and within the wall thickness of the boiler tube. The sensor is designed to adapt to boiler tubes of different diameters by mounting the transducer coils in such a manner that the coils can be pressed against the outer surface of the tubes. In concert, the angle of the acoustic beam between the coils is adjusted by changing the frequency of energy applied to the coils.

In general, the prior efforts in the field have been directed to the use of acoustic sensors or EMAT sensors. Very little effort has been made to create sensor structures appropriate for directing long-range guided-waves into such pipe walls, primarily because of the inability to fully encircle the circumference of the individual pipes. That is, none of the previous efforts that utilize partial circumferential orientation have provided suitable sensor adherence structures for long-range guided-wave inspection purposes. No sensor structures have been designed that can take advantage of the volumetric inspection capabilities of long-range guided-waves where access to the entire circumference of the pipe or tube is restricted. EMAT sensors, such as described in the above U.S. patents, are limited in that they fail to achieve the volumetric inspection capabilities of long-range guided-waves.

It would be desirable, therefore, to have a sensor structure and a method for its implementation, that overcomes many of the problems of existing sensor structures and the requirement that they either fully encircle the pipe or tube under inspection or that they utilize only local point inspection techniques such as ultrasonics or EMAT technologies.

In the present invention, systems and methods for inspecting the fire side of waterwall tubes in boilers, wherein limited access to the entire circumference of the tube is found, are described. The systems and methods are built upon existing magnetostrictive sensor (MsS) methods and devices, particularly the thin magnetostrictive strip approach (described in U.S. Pat. No. 6,396,262, entitled Method and Apparatus for Short Term Inspection or Long Term Structural Health Monitoring; U.S. Pat. No. 6,429,650, entitled Method and Apparatus Generating and Detecting Torsional Wave Inspection of Pipes and Tubes; and U.S. Pat. No. 6,917,196, also entitled Method and Apparatus Generating and Detecting Torsional Wave Inspection of Pipes and Tubes, the disclosures of which are each incorporated herein in their entirety by reference) and a flat coil-type plate magnetostrictive sensor (MsS) (described in U.S. Pat. No. 6,294,912, entitled Method and Apparatus for Non-Destructive Inspection of Plate Type Ferromagnetic Structures Using Magnetostrictive Techniques, the disclosure of which is incorporated herein in its entirety by reference), the structures of which are held in place on the waterwall tubes under the influence of an activatable electromagnetic circuit.

SUMMARY OF THE INVENTION

The present invention therefore describes methods and devices for inspecting waterwall tubes for the detection of fire side damage (wall loss due to erosion and/or corrosion as well as circumferential cracking) over a long length of the tube, in order to rapidly obtain comprehensive condition information about the tube without scanning along the entire tube length. The present invention is a variation of the companion invention disclosure (entitled Method and Device for Long-Range Torsional Guided-Wave Inspection of Piping with a Partial Excitation and Detection around the Pipe Circumference, the subject of co-pending U.S. patent application Ser. No. 11/823,113, filed Jun. 25, 2007) but specifically tailored for waterwall tube applications.

The system of the present invention uses a magnetostrictive strip and a flat coil-type plate magnetostrictive sensor (MsS) that are held in place on the waterwall using a specially designed frame and an electromagnetic circuit. The magnetostrictive strip and plate type MsS are positioned against a tube in the waterwall using an elastomeric pad or a fluid (air or liquid) filled bladder to achieve close contact and good mechanical coupling between the magnetostrictive strip and the tube surface. When current activated, the electromagnet holds the entire assembly in place and provides a DC bias magnetic field required for plate magnetostrictive sensor probe operation. Long-range guided-waves are pulsed into the tube and reflected signals are detected within the same sensor structure. The received signal data representative of a long section of the tube under investigation is then analyzed for the presence of anomalies and defects. When data acquisition for a particular tube or tube section is completed the electromagnet is turned off and the entire device is moved to the next tube in the waterwall. In this manner, a large area of waterwall may be rapidly investigated in its entirety, rather than relying on a statistical sample for predicting the overall condition of the waterwall. Further features of both the system of the present invention and its method of use will become apparent from the following detailed description with reference to the appended drawing figures.

BRIEF DESCRIPTION OF THE DRAWINGS

The accompanying figures will give a fuller description and better understanding of the details and advantages of the present invention. The drawing figures appended may be briefly described as follows.

DETAILED DESCRIPTION OF THE PREFERRED EMBODIMENTS

In general, a preferred method and apparatus for inspecting waterwall tubes for fire side damage according to the present invention, may be summarized as follows:

(a) The placement of a plate type magnetostrictive sensor (MsS) guided-wave probe on the fire side of a waterwall tube, that operates in shear-horizontal (SH) wave mode or, equivalently, torsional (T) wave mode within the tube.

(b) The mechanical coupling of the probe to the tube and the launching of a pulse of guided-waves to one side of the probe (such as upward) along the tube length and the detection of signals reflected from that side. The process is then repeated to launch waves to the other side of the probe (such as downward) and detect the signals reflected from that side.

(c) The analysis of the received signal data for anomalies and defects (cracks, fractures, wall-thinning, etc.).

The various drawing figures briefly described above illustrate schematically a device for inspecting waterwall tubes according to the basic features summarized above. The device is specifically designed to be installed on a waterwall tube and to be supported thereon by the waterwall tubes adjoining the tube under inspection. The device uses a magnetostrictive strip (such as described in U.S. Pat. Nos. 6,396,262, 6,429, 650, and 6,917,196 referenced above and incorporated herein) and a flat-coil type plate MsS (such as described in U.S. Pat. No. 6,294,912 also referenced above and incorporated herein) that are held in place under magnetic force from an electromagnetic circuit.

The magnetostrictive strip and plate type MsS are pressed against the tube with a bladder or elastomeric material to maintain close contact and good mechanical coupling between the sensor and the tube surface. To achieve an appropriate mechanical coupling, the tube wall will typically require sandblasting or other abrasive surface preparation in the local contact area. When activated by the flow of current there through, the electromagnet holds the entire assembly in place and further provides the DC bias magnetization required for optimal plate MsS probe operation. When data acquisition is complete, the electromagnet is turned off and the whole device is moved to the next tube in the waterwall.

Figure 1:
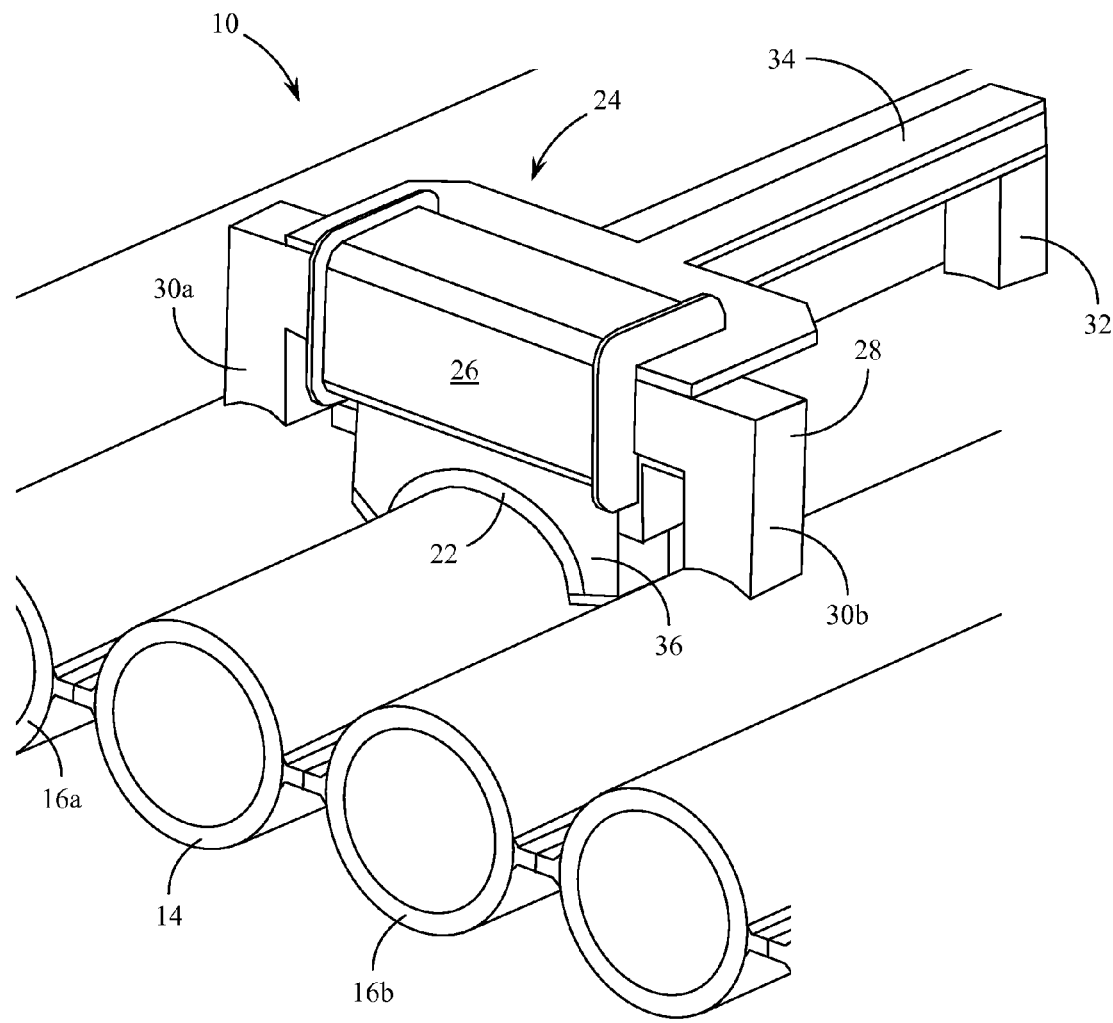
FIG. 1 is a perspective view of the sensor assembly of the present invention positioned in conjunction with the firewall surface of an array of waterwall tubes.

Reference is made to FIG. 1 for a detailed description of the structure of the sensor assembly of the present invention and the manner of its placement and implementation on a typical waterwall panel. Sensor assembly 10 in FIG. 1 is shown in place on waterwall panel 12. It is understood that the orientation of waterwall panel 12 shown in FIG. 1 (i.e., in a horizontal orientation) may not be typical of structures normally encountered in place in operational facilities. Typically, a waterwall might be a vertically oriented panel which provides a primary motivation for the novel attachment features of the sensor assembly of the present invention. That is, one of the primary features of the present invention is the ability to attach the sensor assembly and remove it easily from a vertical structure without requiring physical attachment devices to prevent the sensor from falling off of the vertically oriented wall. It will be understood, however, by those skilled in the art, that the orientation of waterwall 12 is irrelevant to the operation of sensor assembly 10 of the present invention.

In the example shown in FIG. 1 waterwall panel 12 is comprised of an array of parallel, closely spaced tubes. Waterwall tube 14 is the tubular structure that is being subjected to inspection in the example shown in FIG. 1. Adjacent waterwall tubes 16a and 16b each play a role in supporting the structure of sensor assembly 10 as described in more detail below.

Sensor assembly 10 is comprised of a magnetostrictive sensor assembly (described further below) and a larger electromagnet assembly 24. Electromagnet assembly 24 is comprised of electromagnetic coil 26 which surrounds electromagnetic core 28. Extensions of electromagnetic core 28 comprise support feet 30a and 30b which extend at right angles from the core which passes through electromagnetic coil 26. These core and support components preferably comprise metallic or other ferromagnetic materials of high magnetic permeability, that serve to guide the magnetic field generated by electromagnetic coil 26 towards the waterwall, and in particular towards attractive adherence to adjacent waterwall tubes 16a and 16b.

Also extending from electromagnetic core 28 is balance arm 34 which extends to and is supported by balance foot 32. Each of the support feet 30a and 30b as well as balance foot 32 comprise ferromagnetic material such that when electromagnet 24 is activated an attractive magnetic force towards the waterwall is experienced at each of the extensions. As shown in FIG. 1 the face of each of these support structures that is directed toward waterwall panel 12 may have a concave surface that follows the curvature of the convex surface of the outer wall of each of the tubes that make up waterwall panel 12 so as to facilitate this stabile positioning of the sensor assembly 10.

Positioned within a support frame 36 beneath electromagnet assembly 24 are the components that make up the magnetostrictive sensor (MsS) assembly. Support frame 36 is a solid structure that positions a curved face towards waterwall panel 12 as shown. Within this curved face is positioned bladder/elastomeric material 22 that cushions and facilitates the maintenance of close contact between the MsS and the waterwall panel. Bladder/elastomeric material 22 is itself a curved structure, and supports a curved plate type magnetostrictive sensor (MsS) (not seen in FIG. 1 but shown as 20 in FIG. 2) which in turn covers a magnetostrictive strip (also not seen in FIG. 1 but shown as 18 in FIG. 2). Various electrical wires and other conductors necessary for the operation of sensor assembly 10 are omitted from FIG. 1 for clarity. These would include wires directed to electromagnetic coil 26 which may be remotely activated as well as the sensor signal wires which connect to plate magnetostrictive sensor 20. These wires would ultimately extend from sensor assembly 10 and a wiring harness typically with an intermediate releasable connector extends to control instrumentation and data analysis instrumentation as described in more detail below.

Balance arm 34 further provides a convenient mechanism for manipulating sensor assembly 10 during its placement against and removal from waterwall panel 12. A technician might conveniently grasp balance arm 34 and hold sensor assembly 10 in place on the appropriate waterwall tube while activating electromagnet assembly 24. The magnetic field created by electromagnet core 28 would thereafter serve to adhere sensor assembly 10 to waterwall panel 12 while testing occurs. When testing is completed, the technician could once again grasp balance arm 34 and de-activate electromagnet assembly 24 to permit the easy removal of sensor assembly 10 from waterwall panel 12 and the replacement of the same on an adjacent waterwall tube.

Figure 2:
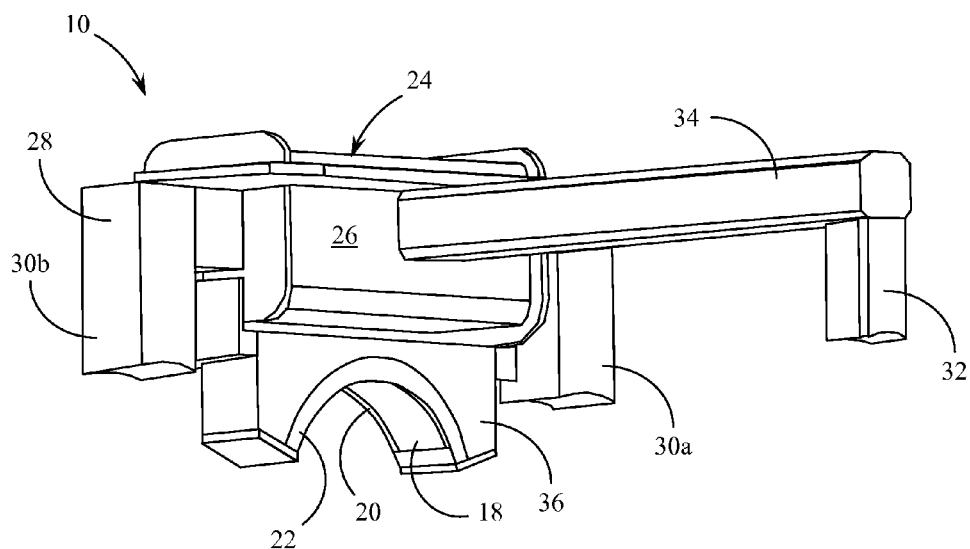
FIG. 2 is a perspective view from a reverse viewpoint (from that of FIG. 1) showing the sensor assembly of the present invention removed from its placement on the firewall to expose the various contact components of the assembly.

Reference is now made to FIG. 2 for a brief description of a view of sensor assembly 10 removed from its placement on a waterwall panel. In this reverse view, the structure and placement of magnetostrictive strip 18 in conjunction with plate magnetostrictive sensor 20 is shown. These sensor components are positioned on and supported by bladder/elastomeric material 22 which itself is supported by sensor support frame 36 which is a rigid curved frame structure positioned beneath electromagnet assembly 24. In this view, balance arm 34 is shown to extend from electromagnetic core 28 to form a tripod assembly in conjunction with support feet 30a and 30b which also extend from electromagnet core 28. Once again, the appropriate electronic/electrical cabling associated with operation of the sensor assembly is not shown in the view in FIG. 2 for clarity.

Figure 3:
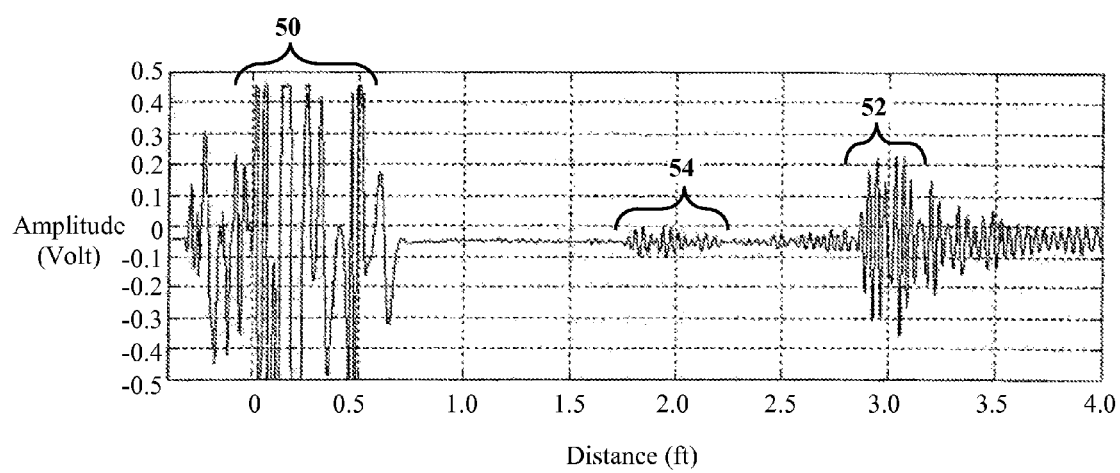
FIG. 3 is a signal plot showing torsional wave data obtained from a tube in a waterwall panel sample using the sensor assembly and methodology of the present invention.

Reference is now made to FIG. 3 for an example of typical signal data acquired with the sensor apparatus and methodology of the present invention. FIG. 3 represents a signal plot showing 150 kHz T-wave (torsional wave) data obtained from a tube in a waterwall panel sample using the method of the present invention. The data shown in FIG. 3 was obtained by placing a plate type magnetostrictive sensor probe near one end of the tube that was approximately 3 feet long and 2 inches in outside diameter. The tube had a typical 0.28 inch wall thickness. The defect established in the tube was a circumferential notch that was approximately 0.6 inches long and 0.11 inches deep at its maximum depth. FIG. 3 shows the signal representative of the initial pulse 50 as well as a return signal representative of the far end 52 of the tube. The defect return signal 54 is seen in the signal plot in FIG. 3 as clearly distinguishable from the balance of the intermediate signal amplitude. The signal plot shown as amplitude versus distance includes, as known in the art, a correlation between signal timing and distance from the signal source based upon the velocity of the signal within the material of the waterwall tube.

It has been observed experimentally that the generated guided-waves, once launched, not only propagate along the tube on the side on which the MsS probe is placed, but also spread out, through the web between the tubes, into the backside of the tube as well as into the adjacent tubes. However, the amount of wave energy transmitted to the backside and the adjacent tubes through the web is shown to be small relative to the wave energy in the probe side of the tube under testing. Therefore, the invented method primarily inspects the fire side of waterwall tubes and the return signal can be identified as reflective of the condition of the tube to which the sensor assembly is specifically fixed.

The inspection range over which defects can be detected depends on the wave frequency and the actual condition of the tube under testing. Generally, however, a 30 to 50 foot inspection range may be achieved in one direction using 100 kHz waves. Since both sides of the probe can be inspected from a given probe location, the entire length of a tube in a waterwall may be inspected from a single testing location.

Figure 4:
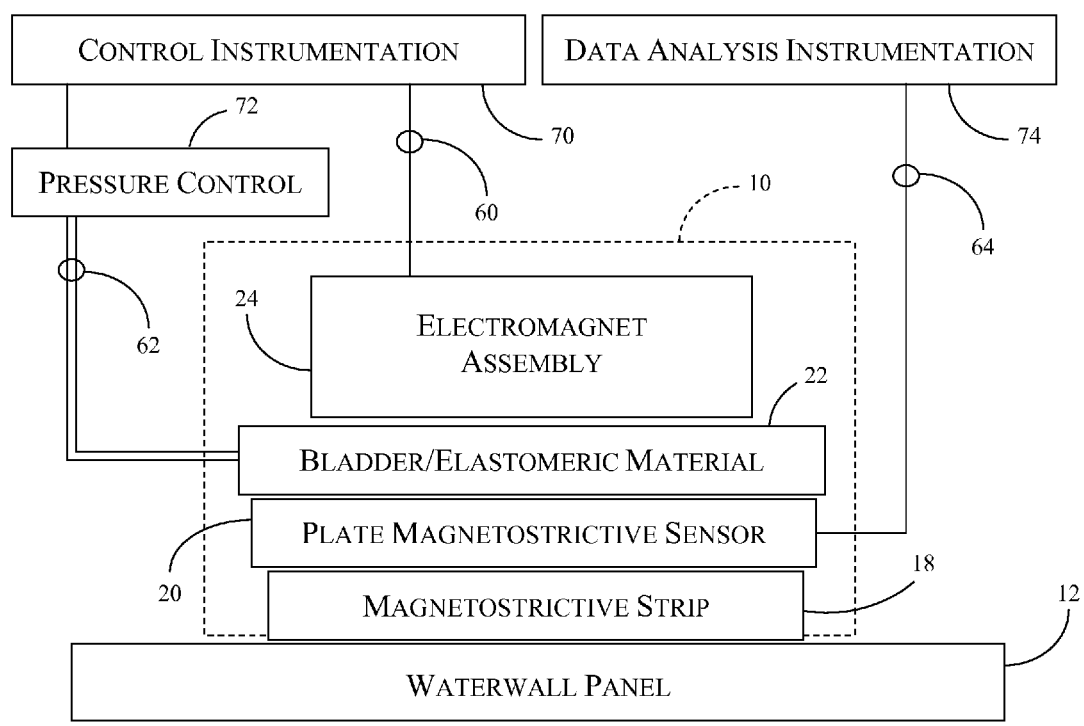
FIG. 4 is schematic block diagram showing the basic mechanical, electronic, and electromagnetic components of the complete system of the present invention.

Reference is now made to FIG. 4 for a brief description of the overall system of the present invention and the functional connections between the various components required to carry out the methodology of the invention. In FIG. 4 waterwall panel 12 is represented as the base structure onto which the sensor assembly 10 (dashed outline) is placed. Sensor assembly 10 is again made up of magnetostrictive strip 18 that forms the contact surface with waterwall panel 12. Plate magnetostrictive sensor 20 is positioned in close proximity to magnetostrictive strip 18 and is supported by bladder/elastomeric material 22. Electromagnet assembly 24 is positioned over the balance of sensor assembly 10 and serves to establish adherence of the sensor assembly to waterwall panel 12 as well as providing the bias magnetic field for optimal sensor operation. In the present application, electromagnet assembly 24 is preferably a DC electromagnet so as to provide a static magnetic field, both for purposes of adherence to the waterwall and the bias magnetic field.

Connections between sensor assembly 10 and the balance of the instrumentation associated with the present invention are also disclosed in FIG. 4. Activation and de-activation of electromagnet 24 is carried out by directing current flow through the coils therein by way of electrical conductors 60 which extend to control instrumentation 70. Plate magnetostrictive sensor 20 is operable through electrical conductor/signal line 64 which connect to data analysis instrumentation 74 for the system.

Bladder/elastomeric material 22 has been described alternately as either a resilient material or an inflatable air or fluid bladder, each of which would facilitate the maintenance of close contact between the magnetostrictive sensor and the waterwall panel. In the embodiment utilizing an air bladder (or fluid bladder) it would be possible and advantageous in certain environments to vary the force exerted by the bladder onto the magnetostrictive sensor components. Reference to "fluid" herein in connection with the bladder will be understood to include both air (gas flow) and liquid. Control of this force could be carried out through the use of a connected port in bladder 22, a connecting pressure line 62, and an appropriate pressure control system 72 that would direct air or fluid into bladder 22 or allow such air or fluid to be released from bladder 22 to vary the force. Control over this functionality could likewise be integrated into control instrumentation 70. As described above, all of the system components associated with sensor assembly 10 are integrated into a handheld device that adheres itself to the waterwall panel. A connecting harness comprising the connecting lines shown in FIG. 4 would extend from the sensor assembly to the instrumentation of the system.

Figure 5:
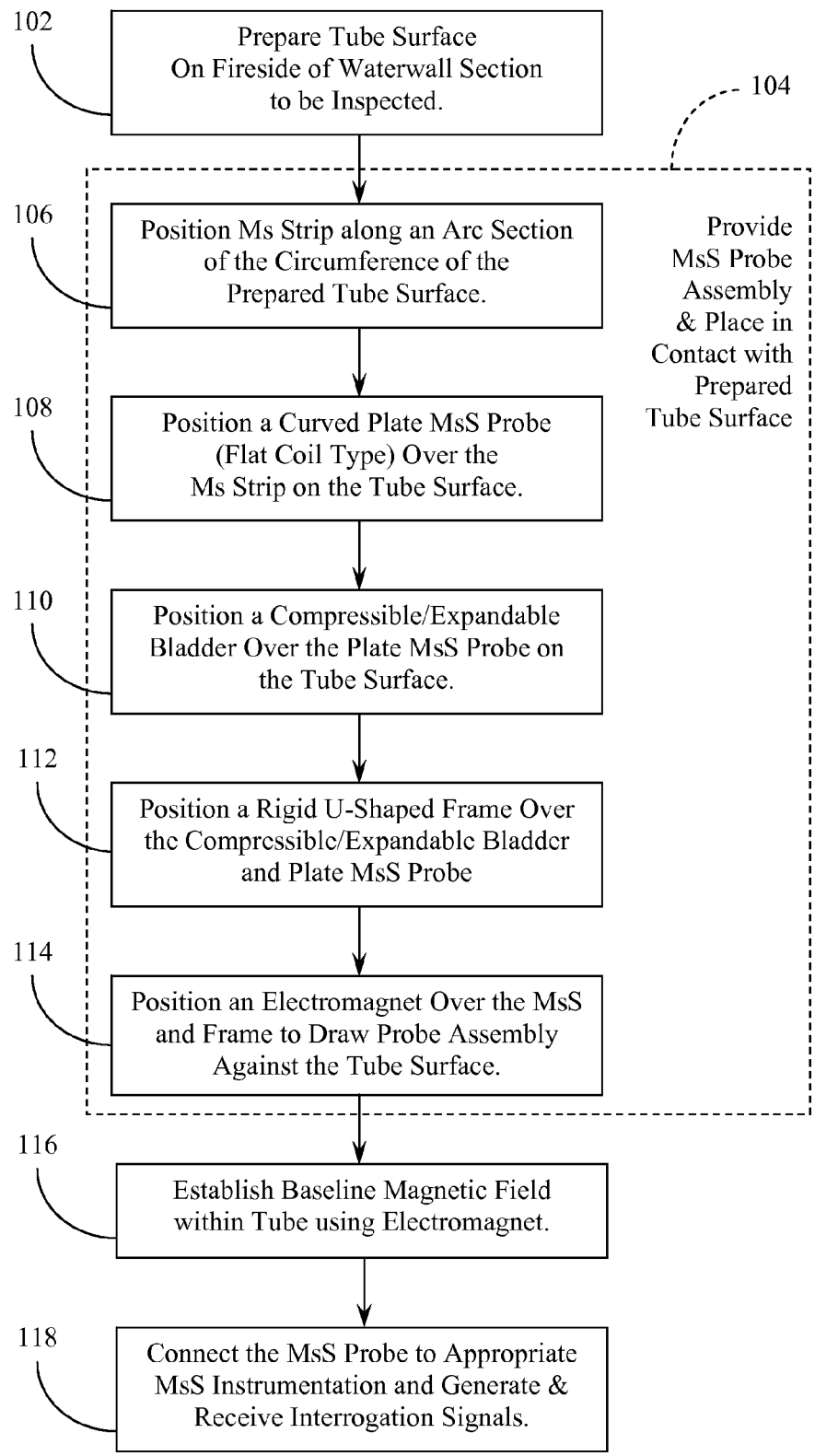
FIG. 5 is a flow chart showing the basic process steps associated with the methodology of implementing the system of the present invention.

Reference is finally made to FIG. 5 for a brief description of the method steps associated with implementation of the system of the present invention. As indicated above, some variations in the methodology will result from structural variations in the configuration of the waterwall panel and the tubes under inspection. In general, however, the process involves preparing the surface of the fire side of the waterwall and providing the apparatus of the present invention to be placed into contact with the tube surfaces within the waterwall.

The process as described in FIG. 5 therefore begins at Step 102 in which a tube surface on the fire side of the waterwall section to be inspected is prepared as by sandblasting or otherwise exposing a contact surface. Step 104, shown in FIG. 5 as being made up of a sequence of steps, collectively defines the step of providing the MsS probe assembly. This step of providing the probe initially comprises, at Step 106, the provision of the Ms strip that is ultimately positioned on the prepared surface of the tube along an arc section of the outer circumference of the tube. Over the Ms strip is positioned, at Step 108, a curved plate MsS probe (flat coil type) and, at Step 110, a compressible/expandable bladder.

At Step 112, a rigid U-shaped frame is positioned over the compressible/expandable bladder and plate MsS probe. As the final step in providing the sensor probe assembly, an electromagnet is positioned over the MsS and frame at Step 114 to draw the probe assembly against the tube surface. It is anticipated that the radius of curvature associated with the individual boiler tubes within a specific waterwall, would directly determine a similar radius of curvature for the Ms strip, the MsS, and the U-shaped frame holding the assembly. The bladder/elastomeric material serves to compensate for modest variations in these curvatures to assure optimal contact with the tube surface.

Once the provided MsS Probe Assembly has been magnetically drawn against the tube surface, then at Step 116, the electromagnet serves to establish a baseline magnetic field within the tube to optimize signal sensitivity. Finally, at Step 118, the MsS probe assembly is connected to appropriate MsS instrumentation (as shown in FIG. 4) and interrogation signals (in the form of T-waves as described above) are directed into the tube and reflected signals are received back for analysis.

Although the present invention has been described in terms of the foregoing preferred embodiments, this description has been provided by way of explanation only and is not intended to be construed as a limitation of the invention. Those skilled in the art will recognize modifications of the present invention and its methods of use that might accommodate specific cylindrical pipe or tube waterwall structures and even specific boiler configurations. Such modifications as to waterwall structures or sensor structures where such modifications are merely incidental to the specific NDE environment do not necessarily depart from the spirit and scope of the underlying invention. As indicated above, it is anticipated that variations in tube diameters would require corresponding variations in the curvature of the contact components described (although various standard sized waterwall tube diameters are known in the art).

The methodology may also differ with variations in boiler configuration. Some boilers may require no more than a single placement of the apparatus of the present invention against a specific tube while other larger boilers might benefit from multiple placements at progressive locations along a single tube. Here again, such variations in methodology do not depart from the spirit and scope of the invention.

We claim:

1. An apparatus for long-range torsional guided-wave inspection of the fire side of a waterwall tube, the apparatus comprising:
    a plate magnetostrictive sensor probe;
    a frame for positioning the plate magnetostrictive sensor probe against an external surface of the waterwall tube;
    a compressible/expandable bladder positioned between the frame and the plate magnetostrictive sensor probe in a manner that directs the magnetostrictive sensor probe against the external surface of the waterwall tube; and
    an electromagnet positioned across the frame in a manner that pulls the frame and the associated bladder and plate magnetostrictive sensor probe against the external surface of the waterwall tube.

2. The apparatus of claim 1 wherein the plate magnetostrictive sensor probe is curved to approximate the outer diameter curvature of the waterwall tube.

3. The apparatus of claim 1 further comprising a strip of magnetostrictive material positioned between the plate magnetostrictive sensor probe and the external surface of the waterwall tube.

4. The apparatus of claim 1 wherein the electromagnet comprises an inverted U-shaped core structure having a plurality of extended feet, wherein the extended feet are structured for direct contact with the external surface of the waterwall tube under inspection and at least one adjacent waterwall tube to facilitate the direction of the magnetic force towards the waterwall tubes.

5. The apparatus of claim 4 wherein the electromagnet core comprises first and second extended feet directed orthogonal to an axis of the waterwall tube under inspection so as to extend to make contact with first and second waterwall tubes adjacent the waterwall tube under inspection.

6. The apparatus of claim 5 wherein the electromagnet core further comprises a third extended foot directed parallel to an axis of the waterwall tube under inspection so as to extend to make contact with the waterwall tube under inspection at a spaced distance from a position of the plate magnetostrictive sensor probe, wherein the three extended feet of the electromagnet core provide a stable tripod support for the sensor probe against the waterwall tubes.

7. The apparatus of claim 6 wherein the third extended foot extends a distance from the electromagnet sufficient to provide a hand grip to permit the manipulation of the apparatus in its placement on and removal from the waterwall tubes.

8. The apparatus of claim 4 wherein the extended feet each comprise curved base surfaces contoured to follow the curvature of the external surface of the waterwall tubes.

9. The apparatus of claim 1 wherein the compressible/expandable bladder comprises a closed cell having a flexible wall and containing a partially compressible material.

10. The apparatus of claim 1 wherein the compressible/expandable bladder comprises a closed cell having at least one port for introducing a fluid into, or removing a fluid from the cell, so as to increase or decrease a fluid pressure within the cell and thereby increase or decrease a force against the plate magnetostrictive sensor probe against the external surface of the waterwall tube.

11. The apparatus of claim 1 further comprising control instrumentation for activating and de-activating the electromagnet so as to alternately draw the plate magnetostrictive sensor probe against the external surface of the waterwall tube or release the probe from the waterwall tubes.

12. The apparatus of claim 1 further comprising data analysis instrumentation for directing an interrogation signal from the plate magnetostrictive sensor probe into the waterwall tube under inspection and analyzing a reflected signal received back from the tube.

13. A method for long-range torsional guided-wave inspection of the fire side of a waterwall tube, the method comprising the steps of:
    providing and positioning a plate magnetostrictive sensor probe over an external surface of the waterwall tube along a portion of a circumference of the tube;
    providing and activating an electromagnet across the plate magnetostrictive sensor probe to draw and maintain the sensor probe into contact with the external surface of the waterwall tube; and
    connecting the magnetostrictive sensor probe to magnetostrictive sensor instrumentation and generating and receiving interrogation signals into and from the waterwall tube under inspection.

14. The method of claim 13 further comprising the step of providing a strip of magnetostrictive material between the plate magnetostrictive sensor probe and the external surface of the waterwall tube.

15. The method of claim 13 further comprising the step of preparing the external surface of the waterwall tube to provide mechanical compliance between the plate magnetostrictive sensor probe and the waterwall tube.

16. The method of claim 14 further comprising the step of establishing a bias magnetic field within the magnetostrictive strip to optimize torsional wave magnetostrictive sensor operation using the activated electromagnet.

17. The method of claim 13 further comprising the steps of:
    providing and positioning a compressible/expandable bladder over the plate magnetostrictive sensor probe; and
    providing and positioning a rigid inverted U-shaped frame over the compressible/expandable bladder and plate magnetostrictive sensor probe.

18. A method for long-range torsional guided-wave inspection of the fire side of a waterwall tube, the method comprising the steps of:
    preparing the external surface of the waterwall tube to provide mechanical compliance between the waterwall tube and a sensor probe to be placed in contact therewith;
    providing and positioning a plate magnetostrictive sensor probe over the prepared external surface of the waterwall tube along a portion of a circumference of the tube;
    providing a strip of magnetostrictive material between the plate magnetostrictive sensor probe and the prepared external surface of the waterwall tube;

providing and positioning a compressible/expandable bladder over the plate magnetostrictive sensor probe;

providing and positioning a rigid inverted U-shaped frame over the compressible/expandable bladder and plate magnetostrictive sensor probe;

providing and activating an electromagnet across the plate magnetostrictive sensor probe to draw and maintain the sensor probe into contact with the external surface of the waterwall tube;

establishing a bias magnetic field within the magnetostrictive strip to optimize torsional wave magnetostrictive sensor operation using the activated electromagnet; and connecting the magnetostrictive sensor probe to magnetostrictive sensor instrumentation and generating and receiving interrogation signals into and from the waterwall tube under inspection.

* * * * *